United States Patent [19]

Ishikawa et al.

[11] 4,286,053

[45] Aug. 25, 1981

[54] PROCESS FOR FORMING DYE IMAGES

[75] Inventors: Wataru Ishikawa; Ryosuke Satoh; Kiyoshi Yamashita; Tugumoto Usui; Katsunori Kato, all of Hino, Japan

[73] Assignee: Konishiroku Photo Industry Co., Ltd., Tokyo, Japan

[21] Appl. No.: 96,452

[22] Filed: Nov. 21, 1979

[30] Foreign Application Priority Data

Nov. 24, 1978 [JP] Japan .................................. 53/145024

[51] Int. Cl.$^3$ .............................................. G03C 7/00
[52] U.S. Cl. ................................... 430/389; 430/557; 430/558
[58] Field of Search ......................... 430/389, 557, 558

[56] References Cited

U.S. PATENT DOCUMENTS

| | | | |
|---|---|---|---|
| 3,891,445 | 6/1975 | Arai et al. | 430/557 |
| 3,960,570 | 6/1976 | Oishi et al. | 430/557 |
| 3,973,968 | 8/1976 | Fujiwhara et al. | 430/558 |
| 4,010,035 | 3/1977 | Fujiwhara et al. | 430/557 |
| 4,057,432 | 11/1977 | Fujiwhara et al. | 430/558 |
| 4,138,263 | 2/1979 | Boie et al. | 430/557 |

FOREIGN PATENT DOCUMENTS 47-24321 of 1972 Japan .

*Primary Examiner*—J. Travis Brown
*Attorney, Agent, or Firm*—Bierman & Bierman

[57] ABSTRACT

Process for forming yellow dye images in silver halide photographic material using 2-equivalent α-pivaloyl acetanilide couplers having at the 5-position a ballasting sulfonyl amido group.

13 Claims, No Drawings

PROCESS FOR FORMING DYE IMAGES

This invention relates to a process for forming dye images using a light-sensitive silver halide photographic material and more particularly is concerned with a process for forming dye images using in the photographic material novel active point substitution type yellow couplers which are excellent in color developability, free from color stain, excellent in stability against exposure to light and capable of being synthesized at low cost.

Light-sensitive silver halide photographic materials of a silver saving type were directed to and developed and some processes have already been proposed. As disclosed, for example, in Japanese Patent Publication No. 13576/1974, there is known a process using a so-called 2-equivalent type coupler, said coupler being prepared by introducing a substituent into the active point of a color coupler so that the use of 2 silver atoms is made sufficient to form one molecule of a dye while the use of 4 silver atoms was necessary in the case of conventional so-called 4-equivalent type coupler. According to this process, it is possible in fact to reduce the amount of silver necessary in the 2-equivalent type coupler to one half of that used in the conventional 4-equivalent type coupler because the 2-equivalent type coupler is high in silver utilizing efficiency as compared with the 4-equivalent type coupler. For this reason, therefore, 2-equivalent type couplers are much used in recent years.

On the other hand, a process for forming dye images is already well known, in which a light-sensitive silver halide photographic material containing color couplers, irrespective of 2-equivalent or 4-equivalent type, after imagewise exposure to light, is developed with a color developer containing an aromatic primary amine type developing agent. Of the color couplers used in this process, the yellow couplers generally have active methylene groups which are serviciable to said couplers in forming yellow dyes on coupling with an oxidation product of the aromatic primary amine type developing agent.

In this connection, the yellow couplers most practically used are those of an α-acetanilide type and, above all, α-pivaloyl-2-chloracetanilide type yellow couplers having ballast components at the 5-position are excellent in storability particularly light fastness, i.e. stability against light exposure, as compared with yellow couplers of different structures. However, since the yellow couplers of the type have a weak color developability and poor practical usefulness when they are used as the 4-equivalent type couplers, the aforesaid technique of using the yellow couplers as the 2-equivalent type couplers was developed, and thus the 2-equivalent type yellow couplers have been put into practice nowadays, winning a reputation as excellent color couplers.

In the aspect of development of light-sensitive silver halide photographic materials containing yellow couplers, on the other hand, it has heretofore been practiced to enhance color developing efficiency in the photographic materials under development by the use of conventional color developers having incorporated therein benzyl alcohol. However, the use of benzyl alcohol in the color developer causes a serious problem of environmental pollution, for example, increased values of B.O.D. (biochemical oxygen demand) or the like. Under the circumstances, it has now been hoped that yellow couplers which can exhibit their sufficient color developability in the course of color development even in the presence of a color developer containing benzyl alcohol reduced in amount.

In the step of color development using a color developer with a reduced amount of benzyl alcohol, however, almost all of the conventionally known α-pivaloyl-2-chloroacetanilide type 2-equivalent yellow couplers having at the 5-position the ballast components are poor in color developability and there are observed many cases where photographic characteristics of the photographic material, after color development, are profoundly influenced by virtue of slight changes in amount of a high boiling solvent in which the yellow coupler has been dispersed. In case a N-substituted or unsubstituted alkylsulfonamido or arylsulfonamido group has been introduced into the ballat component at the 5-position of the above-mentioned 2-equivalent yellow coupler, color developability (maximum density) of the coupler is found to have been improved, though the improvement is not to a sufficient extent. In that case, however, there are involved such problems as increment in fog density and color stain caused by the introduction of such group as mentioned above, marked deterioration in storability (particularly light fastness) associated with the introduction of the alkoxycarbonyl group or the N-substituted or unsubstituted alkylsulfonamido or arylsulfonamido group, or high costs of starting materials for the yellow couplers of this type or inapplicability of said yellow couplers to a process for the synthesis on a large industrial scale or difficulty in purification thereof.

Accordingly, an object of the present invention is primarily to provide novel yellow couplers to be used in a process for forming dye images by color development of light-sensitive silver halide photographic materials, which couplers are found favorable in color developability even when the amount of benzyl alcohol to be contained in a color developer is reduced and give sufficient maximum density, and which do not exert any great adverse influence on photographic characteristics even when the amount of a high boiling solvent having dispersed therein the yellow coupler is changed and which attain atable color developability and, moreover, impart excellent light fastness to the dye images obtained by the color development.

The object of the present invention is secondarily to provide novel yellow couplers which can be synthesized in high purity by a simple process using unexpensive and readily available strating materials therefor.

The object of the present invention is thirdly to provide light-sensitive silver halide photographic materials capable of forming desirable dye images by the use of the novel yellow couplers and a process for forming the desirable dye images.

The above-mentioned objects of the present invention can be attained by a yellow coupler represented by the following general formula (I)

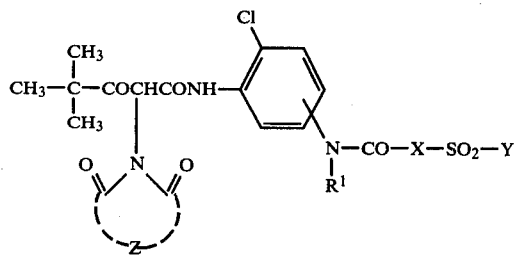

In the above formula, R[1] represents a hydrogen atom, an alkyl group (e.g. methyl, ethyl, dodecyl), aryl group (e.g. phenyl, naphthyl) or heterocyclic residue (e.g. pyridyl, pyrazinyl, furyl), and these alkyl, aryl or heterocyclic groups may individually have a substituent. Though not particularly limited, typical of the above-mentioned substituent are a halogen atom (e.g. fluorine, chlorine, bromine and iodine), alkyl group (e.g. methyl, ethyl, t-butyl), aryl group (e.g. phenyl, p-chlorophenyl, p-methoxyphenyl, p-dodecylphenyl, naphthyl), alkoxy group (e.g. methoxy, ethoxy, t-butoxy, benzyloxy, dodecyloxy), aryloxy group (phenoxy, etc.), alkylthio group (ethylthio, hexylthio, etc.), arylthio group (phenylthio, etc.), alkylsulfonyl group (β-hydroxyethylsulfonyl, dodecylsulfonyl, etc.), arylsulfonyl group (phenylsulfonyl, etc.), acylamino, carbamoyl, acyl, sulfonamido, sulfamoyl, nitrile and the like groups. R[1] is preferably a hydrogen atom. Z represents a non-metal atomic group necessary for forming, in cooperation with —CO—N—CO—, a 5- or 6-membered ring.

The 5- or 6-membered ring residue formed herein in the above manner is a substituent component to be introduced into the active point, typical of which are, for example, 2,5-dioxo-imidazolidine, 2,3,5-trioxoimidazolidine, 2,5-dioxotriazolidine, 2,4-oxazolidine-dione, 2,4-thiazolidine-dione or the like derivatives from which one hydrogen atom has been removed. X represents an alkylene group (e.g. methylene, ethylene, 2-phenylethylene, p-chlorophenylmethylene), arylene group (e.g. phenylene, naphthylene), divalent group in which an alkylene and arylene groups have been bonded together (this divalent group called an aralkylene group which includes p-phenylmethylene, etc.) or divalent organic group represented by the following general formula (II), which individually have a substituent, and preferably X is an alkylene group which may have a substituent. As a substituent for X, there may be mentioned such groups as mentioned in the case of R[1]. Y represents an alkyl group (e.g. ethyl, propyl, dodecyl), aryl group (e.g. phenyl, dodecylphenyl, dodecyloxyphenyl) or heterocyclic residue (e.g. pyridyl, pirazinyl, furyl), which may individually have a substituent, and preferably Y is an alkyl or aryl group which may individually have a substituent. As a substituent for Y, there may be mentioned such atoms or groups as exemplified in the case of R[1].

General formula (II)

—A—V—B—

In the above formula, A and B individually represent an alkylene group (e.g. methylene, propylmethylene, trimethylene), arylene group (e.g. phenylene, naphthylene) or divalent group in which an alkylene and arylene groups have been bonded together (e.g. p-phenylenemethylene), which individually have a substituent.

As a substituent for A as well as for B, there may be mentioned such atoms or groups as exemplified in the case of R[1].

V represents a divalent linking group (e.g. an oxy, thio, carboxyamide, sulfoamide and ureylene group).

Typical examples of the yellow coupler represented by the general formula (I) used in the present invention (hereinafter called "the present yellow coupler") are exemplified below. The present yellow couplers thus exemplified, however, are given for not limitative but illustrative purposes.

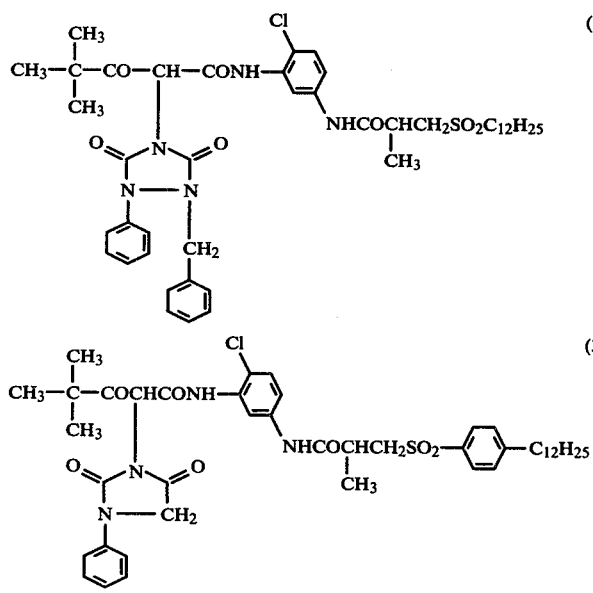

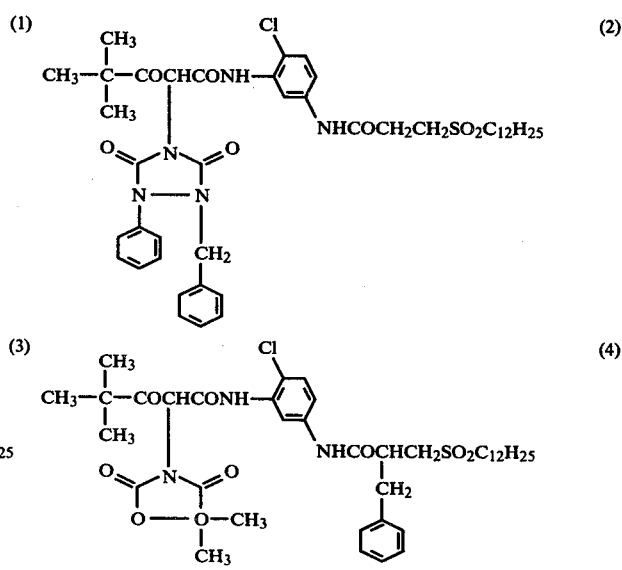

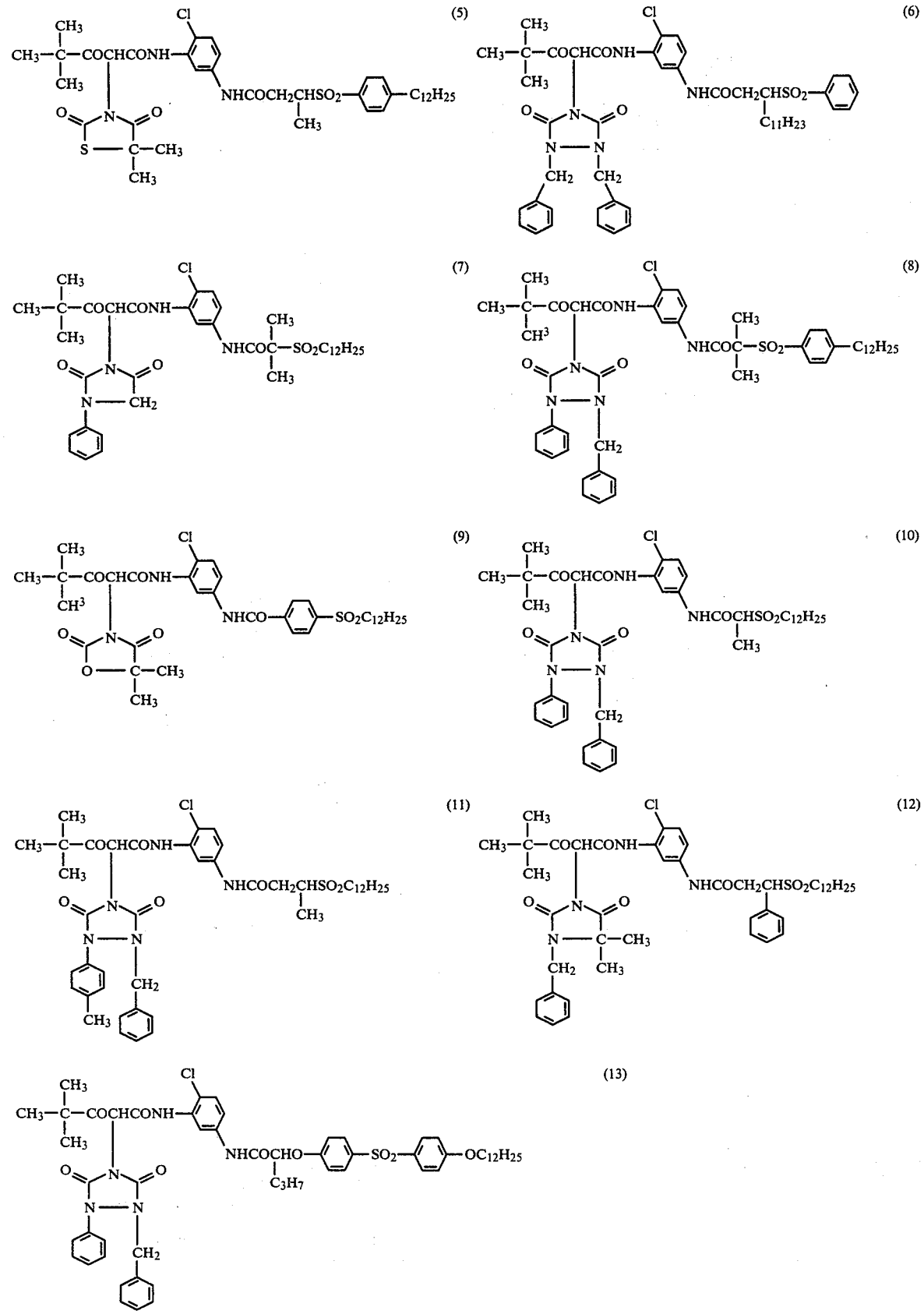

-continued
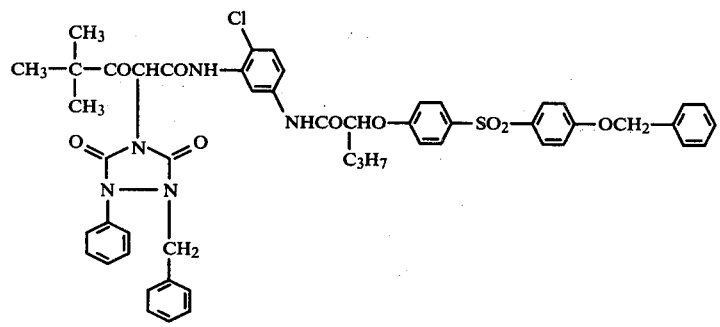
(14)
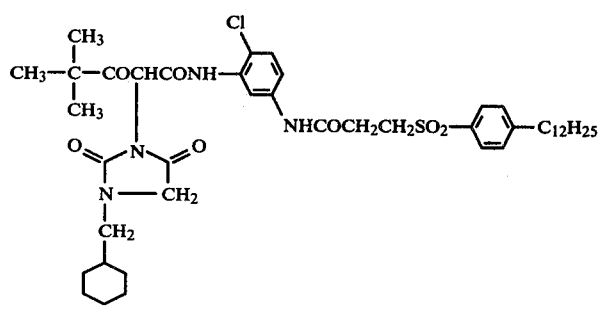
(15)
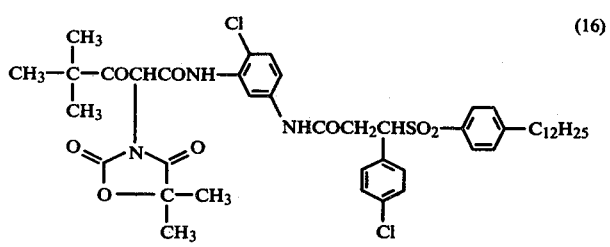
(16)
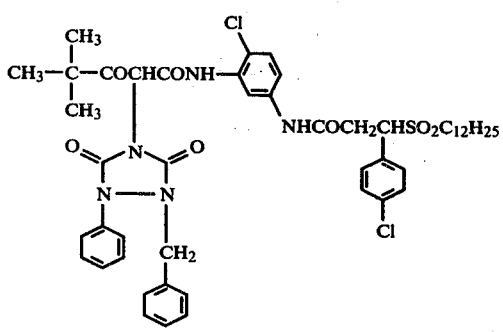
(17)
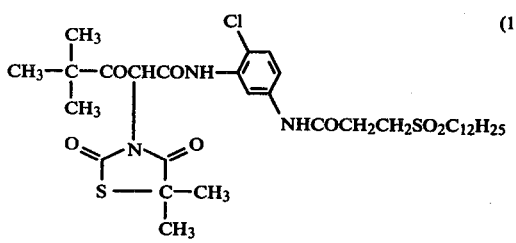
(18)
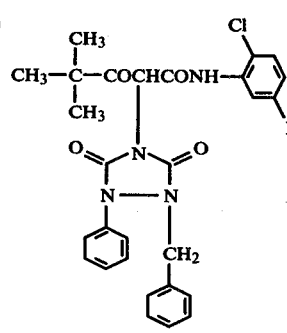
(19)
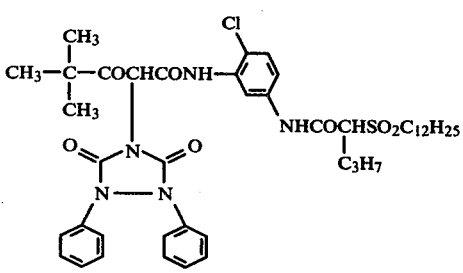
(20)
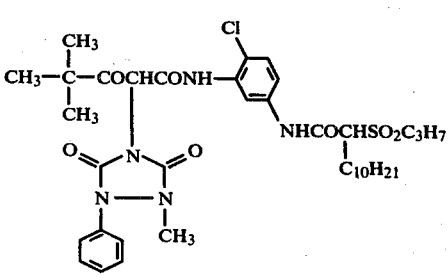
(21)

-continued
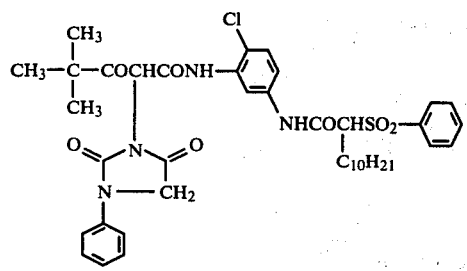 (22)
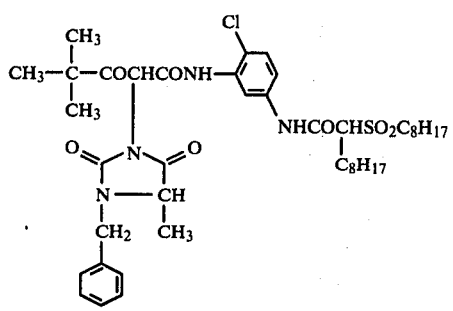 (23)
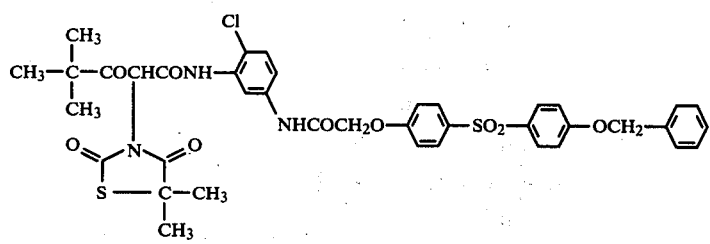 (24)
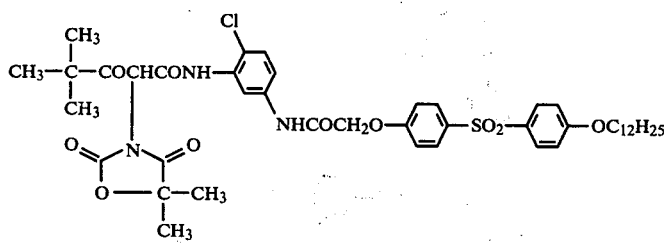 (25)
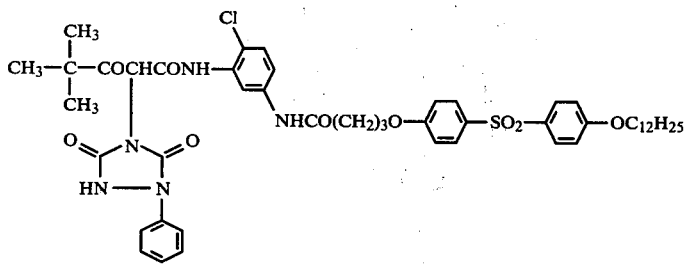 (26)
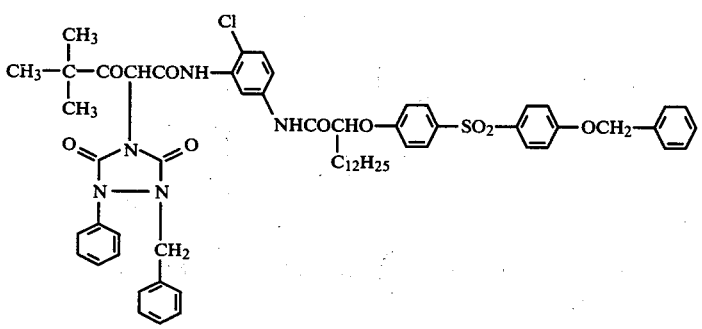 (27)
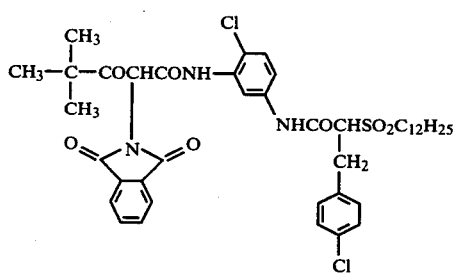 (28)
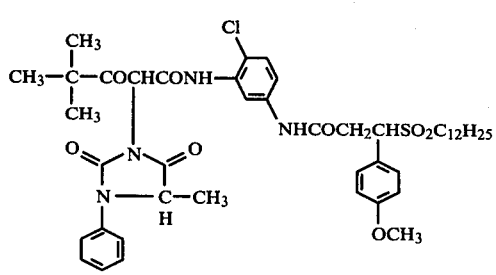 (29)

-continued
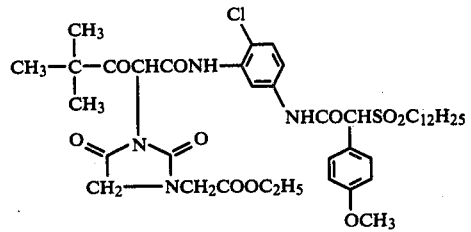 (30)
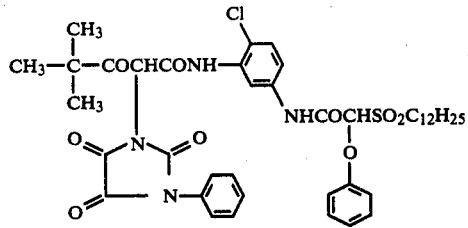 (31)
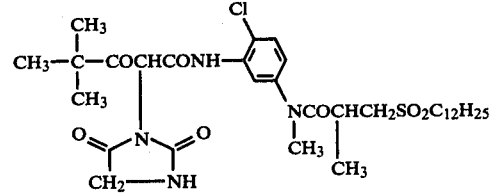 (32)
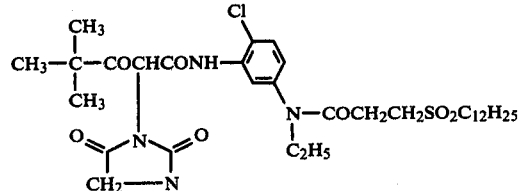 (33)
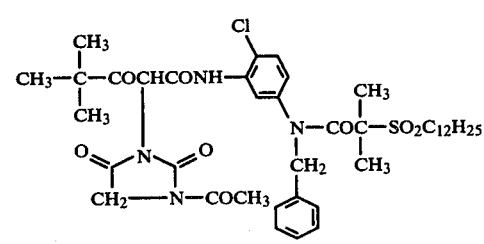 (34)
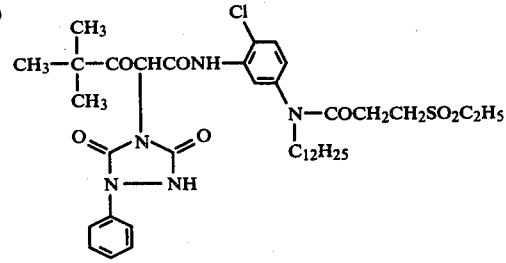 (35)
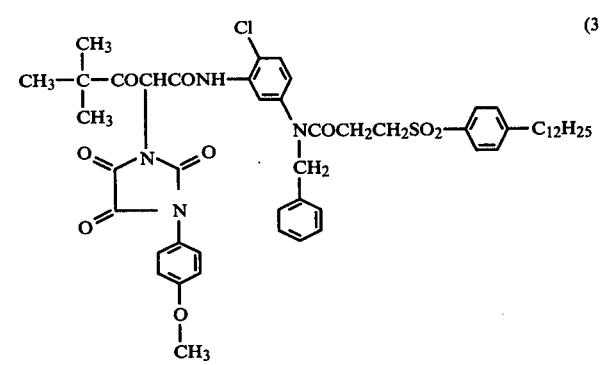 (36)
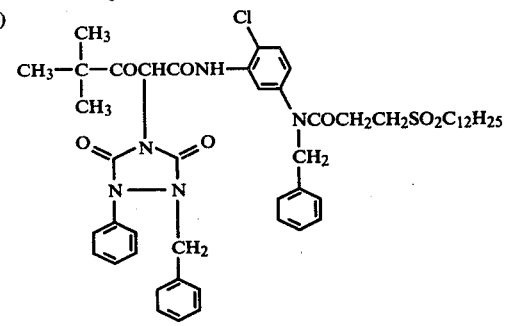 (37)
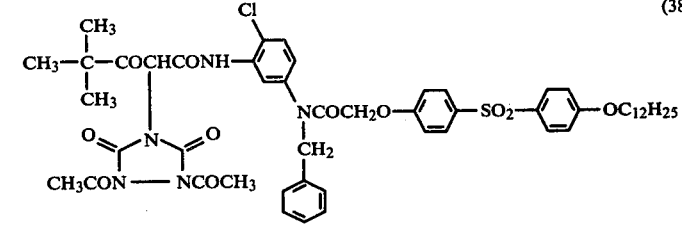 (38)
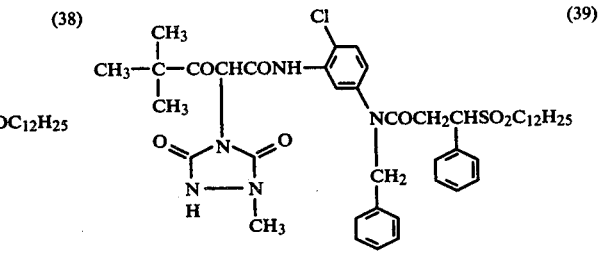 (39)
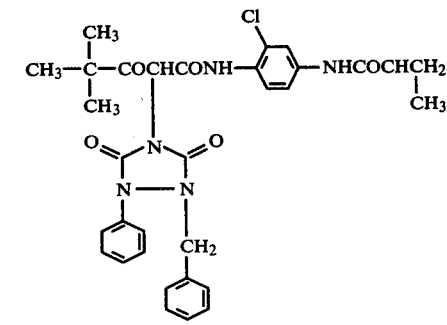 (40)
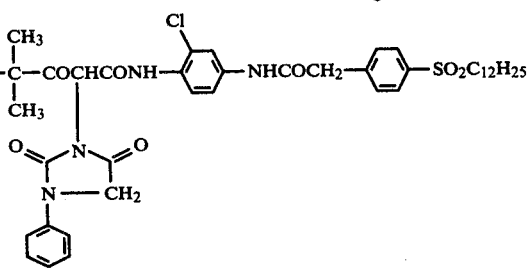 (41)

Typical yellow couplers of the present invention are illustrated below with reference to synthesis examples thereof.

Elementary analysis values of the present yellow couplers exemplified in the synthesis examples are shown, together with those of other exemplified couplers, in a table given later subsequent to explanations of the synthesis examples.

SYNTHESIS EXAMPLE 1

α-Pivaloyl-α-[1-(3-benzyl-4-phenyl-2,5-dioxo-1,3,4-triazolidinyl)]-2-chloro-5-(α-methyl-β-dodecylsulfonylpropionamido)acetanilide

[Synthesis of exemplified coupler 1)]

In 5,000 ml of acetonitrile, 534 g of α-pivalyl-α-[1-(3-benzyl-4-phenyl-2,5-dioxo-1,3,4-triazolidinyl)]-2-chloro-5-aminoacetanilide and 340 g of α-methyl-β-dodecylsulfonylpropionic acid chloride (a compound disclosed in Japanese Laid-Open-to-Public Publn. No. 24321/1972) are refluxed with stirring for 2 hours. Recrystallization from 1,000 ml of methanol, after distilling off the acetonitrile under reduced pressure, gives 784 g of the title product, m.p. 126°–127° C.

SYNTHESIS EXAMPLE 2

α-Pivaloyl-α-[1-(3-benzyl-4-phenyl-2,5-dioxo-1,3,4-triazolidinyl)]-2-chloro-5-(β-dodecylsulfonylpropionamido)acetaniled

[Synthesis of exemplified coupler 2)]

Synthesis Example 1 is repeated, except that 326 g of β-dodecylsulfonylpropionic acid chloride is used in place of the α-methyl-β-dodecylsulfonylpropionic acid chloride, followed by the same process as in Synthesis Example 1, to obtain 780 g of the title product, m.p. 130°–131° C.

SYNTHESIS EXAMPLE 3

α-Pivaloyl-α-[1-(3-benzyl-4-phenyl-2,5-dioxo-1,3,4-triazolidinyl)]-2-chloro-5-(N-benzyl-β-dodecylsulfonylpropionamido)acetanilide

[Synthesis of exemplified coupler 37)]

Synthesis Example 2 is repeated, except that 624 g of α-pivalyl-α-[1-(3-benzyl-4-phenyl-2,5-dioxo-1,3,4-triazolidinyl)]-2-chloro-5-(N-benzylamino)acetanilide is used in place of the α-pivalyl-α-[1-(3-benzyl-4-phenyl-2,5-dioxo-1,3,4-triazolidinyl)]-2-chloro-5-aminoacetanilide, followed by the same process as in Synthesis Example 2, to obtain 763 g of the title product, m.p. 120°–122° C.

SYNTHESIS EXAMPLE 4

α-Pivaloyl-α-(2-phenyl-2,5-dioxo-1-imidazolidinyl)-2-chloro-5-(α-dodecylsulfo-α-methylpropionamido)acetanilide

[Synthesis of exemplified coupler 7)]

A mixture of 404 g of dodecylmercaptan and 46 g of metallic sodiun is stirred at 100°–120° C. for 1 hour and then allowed to cool, whereupon crystallization is induced. The crystallized product is dissolved in 2,000 ml of alcohol and refluxed with stirring for 4 hours, while adding dropwise thereto 392 g of ethyl ester of α-bromo-α-methylpropionic acid. After filtration and concentration, the concentration is distilled under reduced pressure to obtsin 570 g of α-dodecylthio-α-methylpropionic acid ethyl ester, b.p. 150°–152° C./1 mmHg.

To a solution of 200 g of KOH in 1680 ml of alcohol and 1120 ml of water is added 570 g of the ester obtained above and refluxed with stirring for 2 hours. The resulted liquid is acidified with hydrochloric acid, followed by addition with ice-cold water, and the deposited crystals are collected by filtration. Recrystallization from 1,000 ml of methanol gives 380 g of α-dodecylthio-α-methylpropionic acid, m.p. 62°–64° C.

To a solution of 380 g of the thus obtained propionic acid in 1,300 ml of acetic acid is dropwise added at 70°–80° C. 620 g of a 35% hydrogen peroxide solution, followed by refluxing for 1 hour. The reaction liquid is poured into ice-cold water and deposited ceystals are collected by filtration. Recrystallization from 2,000 ml of a 80% methanol gives 348 g of α-dodecylsulfo-α-methylpropionic acid, m.p. 84°–85° C.

A mixture of 200 ml of thionyl chloride and 325 g of the above-obtained propionic acid is refluxed for 1 hour and, after removal of the excess of the thionyl chloride by distillation under reduced pressure, 100 ml of acetonitrile is added thereto to obtain an acetonitrile solution of the acid chlorode.

To a solution of 443 g of α-pivaloyl-α-(3-phenyl-2,5-dioxo-1-imidazolidinyl)-2-chloro-5-aminoacetanilide in 5,000 ml of acettonitrile is added the thus obtained acetonitrile solution of the acid chloride, followed by refluxing with stirring for 2 hours. After distilling off the acetonitrile under reduced pressure, the residue is recrystallized from 1,000 ml of methanol to obtain 620 g of the title product, m.p. 86°–88° C.

Exemplified couplers of the present invention other than those illustrated above were also found to be capable of being synthesized by the same processes as mentioned above or procedures similar thereto.

Thus, the couplers of the present invention can readily by synthesized using inexpensive starting materials.

TABLE

| Coupler No. | | C (%) | H (%) | N (%) | S (%) | Cl (%) |
|---|---|---|---|---|---|---|
| 1 | Calculated | 63.17 | 6.98 | 8.37 | 3.83 | 4.23 |
|   | Found | 63.25 | 6.90 | 8.46 | 3.88 | 4.25 |
| 2 | Calculated | 62.79 | 6.86 | 8.51 | 3.89 | 4.31 |
|   | Found | 62.86 | 6.92 | 8.49 | 3.95 | 4.29 |
| 3 | Calculated | 64.32 | 6.99 | 6.82 | 3.90 | 4.31 |
|   | Found | 64.40 | 6.78 | 6.75 | 3.92 | 4.28 |
| 4 | Calculated | 62.03 | 7.28 | 5.42 | 4.14 | 4.57 |
|   | Found | 61.91 | 7.36 | 5.41 | 4.04 | 4.60 |
| 5 | Calculated | 60.77 | 7.14 | 5.31 | 8.11 | 4.48 |
|   | Found | 60.82 | 7.18 | 5.39 | 8.06 | 4.45 |
| 6 | Calculated | 65.49 | 6.73 | 7.79 | 3.56 | 3.94 |
|   | Found | 65.52 | 6.78 | 7.84 | 3.47 | 3.93 |
| 7 | Calculated | 61.22 | 7.16 | 7.51 | 4.30 | 4.75 |
|   | Found | 61.15 | 7.11 | 7.56 | 4.22 | 4.76 |
| 8 | Calculated | 65.80 | 6.84 | 7.67 | 3.51 | 3.88 |
|   | Found | 65.88 | 6.88 | 7.59 | 3.46 | 3.81 |
| 9 | Calculated | 60.68 | 6.88 | 5.73 | 4.37 | 4.84 |
|   | Found | 68.75 | 6.94 | 5.65 | 4.32 | 4.80 |
| 10 | Calculated | 62.79 | 6.86 | 8.51 | 3.89 | 4.31 |
|   | Found | 62.71 | 6.76 | 8.61 | 3.94 | 4.33 |
| 11 | Calculated | 63.54 | 7.11 | 8.23 | 3.77 | 4.16 |
|   | Found | 63.65 | 7.26 | 8.16 | 3.72 | 4.20 |
| 12 | Calculated | 65.04 | 7.22 | 6.59 | 3.77 | 4.17 |
|   | Found | 65.18 | 7.16 | 6.64 | 3.71 | 4.22 |
| 13 | Calculated | 66.16 | 6.62 | 6.76 | 3.09 | 3.42 |
|   | Found | 66.25 | 6.73 | 6.62 | 3.18 | 3.31 |
| 14 | Calculated | 65.29 | 5.26 | 7.32 | 3.35 | 3.70 |
|   | Found | 65.41 | 5.38 | 7.41 | 3.39 | 3.65 |
| 15 | Calculated | 64.32 | 6.99 | 6.82 | 3.90 | 4.31 |
|   | Found | 64.48 | 7.07 | 6.88 | 3.99 | 4.23 |
| 16 | Calculated | 62.05 | 6.59 | 4.82 | 3.68 | 8.14 |
|   | Found | 62.18 | 6.65 | 4.62 | 3.74 | 8.19 |
| 17 | Calculated | 63.07 | 6.37 | 7.50 | 3.43 | 7.60 |
|   | Found | 63.16 | 6.24 | 7.56 | 3.36 | 7.55 |
| 18 | Calculated | 56.59 | 7.19 | 5.99 | 9.15 | 5.06 |
|   | Found | 56.68 | 7.20 | 5.97 | 8.97 | 4.92 |

TABLE-continued

| Coupler No. | | C (%) | H (%) | N (%) | S (%) | Cl (%) |
|---|---|---|---|---|---|---|
| 19 | Calculated | 59.09 | 6.61 | 7.65 | 7.01 | 3.87 |
|    | Found      | 59.11 | 6.79 | 7.50 | 6.84 | 3.75 |
| 20 | Calculated | 63.17 | 6.98 | 8.37 | 3.83 | 4.23 |
|    | Found      | 63.25 | 7.04 | 8.44 | 3.76 | 4.25 |
| 21 | Calculated | 59.53 | 7.02 | 9.38 | 4.29 | 4.75 |
|    | Found      | 59.42 | 7.11 | 9.48 | 4.39 | 4.68 |
| 22 | Calculated | 62.76 | 6.45 | 7.32 | 4.18 | 4.63 |
|    | Found      | 62.89 | 6.62 | 7.25 | 4.26 | 4.69 |
| 23 | Calculated | 62.93 | 7.67 | 6.99 | 4.00 | 4.42 |
|    | Found      | 62.81 | 7.53 | 7.08 | 3.89 | 4.54 |
| 24 | Calculated | 59.11 | 4.83 | 5.30 | 8.09 | 4.47 |
|    | Found      | 59.29 | 4.94 | 5.38 | 7.96 | 4.41 |
| 25 | Calculated | 61.84 | 6.60 | 4.91 | 3.75 | 4.14 |
|    | Found      | 61.96 | 6.67 | 5.04 | 3.62 | 4.08 |
| 26 | Calculated | 63.24 | 6.49 | 7.52 | 3.44 | 3.81 |
|    | Found      | 63.38 | 6.61 | 7.46 | 3.49 | 3.94 |
| 27 | Calculated | 67.66 | 6.33 | 6.46 | 2.96 | 3.27 |
|    | Found      | 67.83 | 6.47 | 6.58 | 3.09 | 3.30 |
| 28 | Calculated | 62.05 | 6.32 | 5.16 | 3.94 | 8.72 |
|    | Found      | 62.11 | 6.39 | 5.24 | 3.99 | 8.75 |
| 29 | Calculated | 63.47 | 6.98 | 6.58 | 3.76 | 4.16 |
|    | Found      | 63.56 | 7.04 | 6.62 | 3.71 | 4.14 |
| 30 | Calculated | 59.08 | 6.89 | 6.72 | 3.84 | 4.25 |
|    | Found      | 59.12 | 6.95 | 6.81 | 3.88 | 4.26 |
| 31 | Calculated | 61.26 | 6.24 | 6.80 | 3.89 | 4.30 |
|    | Found      | 61.33 | 6.30 | 6.84 | 3.92 | 4.27 |
| 32 | Calculated | 58.00 | 7.52 | 8.19 | 4.69 | 5.18 |
|    | Found      | 57.87 | 7.40 | 8.09 | 4.73 | 5.20 |
| 33 | Calculated | 58.55 | 7.66 | 8.03 | 4.59 | 5.08 |
|    | Found      | 58.46 | 7.81 | 7.97 | 4.52 | 5.04 |
| 34 | Calculated | 61.44 | 7.16 | 6.99 | 4.00 | 4.42 |
|    | Found      | 61.32 | 7.11 | 7.06 | 3.96 | 4.39 |
| 35 | Calculated | 60.02 | 7.15 | 9.21 | 4.21 | 4.66 |
|    | Found      | 59.90 | 7.07 | 9.29 | 4.16 | 4.59 |
| 36 | Calculated | 65.05 | 6.53 | 5.95 | 3.40 | 3.76 |
|    | Found      | 65.17 | 6.58 | 5.99 | 3.36 | 3.72 |
| 37 | Calculated | 65.80 | 6.84 | 7.67 | 3.51 | 3.88 |
|    | Found      | 65.72 | 6.78 | 7.72 | 3.44 | 3.92 |
| 38 | Calculated | 62.41 | 6.24 | 6.99 | 3.20 | 3.54 |
|    | Found      | 62.45 | 6.29 | 7.06 | 3.29 | 3.48 |
| 39 | Calculated | 63.17 | 6.98 | 8.37 | 3.83 | 4.23 |
|    | Found      | 63.24 | 7.11 | 8.45 | 3.75 | 4.19 |
| 40 | Calculated | 63.17 | 6.98 | 8.37 | 3.83 | 4.23 |
|    | Found      | 63.26 | 7.16 | 8.42 | 3.80 | 4.25 |
| 41 | Calculated | 63.57 | 6.73 | 7.06 | 4.04 | 4.46 |
|    | Found      | 63.71 | 6.82 | 7.01 | 4.12 | 4.43 |

The yellow couplers of the present invention as illustrated above are usable either singly or in combination of two or more.

The present yellow couplers are useful as so-called protect-dispersed type couplers which are used in the form of their solutions in a high boiling organic solvent having a boiling point of above 175° C. and hardly miscible with water, for example, dibutyl phthalate, tricresyl phosphate or the like. Further, the present yellow couplers are also usable after dissolving them simply in a substantially water-insoluble low boiling organic solvent, such as ethyl acetate, butyl acetate or the like, or in a water soluble low boiling organic solvent, such as methanol, ethanol, methyl cellosolve, methyl isobutyl ketone or the like. The present yellow couplers are also usable as couplers used in the so-called diffusion transfer process for forming transfer images on an image receiving element by bringing a photosensitive element having a photosensitive layer into contact with a processing sheet.

Furthermore, the present yellow couplers are also applicable to dye image forming processes as disclosed in Japanese Patent Publn. No. 26585/1974, U.S. Pat. No. 3,486,890 or Research Disclosure Nos. 12044 and 12840. That is, a light-sensitive silver halide photographic material having incorporated therein the present yellow coupler and an aromatic primary amine developing agent, after imagewise exposure to light, is subjected to color development by treatment with an alkaline black-and-white developer or by heat treatment, whereupon a dye image favorable in gradation is obtained.

In the manner explained above, the present yellow couplers can form yellow dye images according to a variety of processes and can attain the expected obects of the present invention in each of the processes to which the present yellow couplers are applied.

In the present yellow couplers, the ballast group thereof encompasses the same ballast components as those of the yellow couplers disclosed in Japanese Laid-Open-to-Public Publn. No. 24321/1972. However, α-pivalyl-2-chloro-(α-methyl-β-dodecylsulfonylpropionamido)acetanilide (exemplified compound 2) disclosed in said Publication is a 4-equivalent type yellow coupler, though it is similar at a glance in chemical structure to that of the present yellow couplers, and at present is not excellent from practical point of view as α-pivalyl-2-chloroacetanilide type yellow coupler having the ballast component at the 5-position. As is clear from Example 3 of the present invention mentioned later, moreover, it is understood that out of α-pivalyl-2-chloro-2-acetanilide type yellow couplers of the 4-equivalent type having the ballast component at the 5-position, the yellow coupler disclosed in the above-mentioned publication is not particularly excellent in color developability in color development using a color developer, the benzyl alcohol content of which has been reduced to less than 1/5 of benzyl alcohol usually used, i.e. the amount of benzyl alcohol used being less than 1 ml per liter of the color developer.

As is clear from Example 1 or 2 of the present specification, however, it is understood that in color development using the reduced amount of benzyl alcohol, the 2-equivalent type couplers of the present invention are excellent in color developability and further excellent in storability (light fastness). Such fact cannot be anticipated at all from any existing known references. As is clear from Examples 4 and 5, it is understood that the present yellow couplers are excellent in solubility and dispersion stability in high boiling solvents and exhibit stable color developability without being greatly influenced on photographic characteristics by changes in amount of the high boiling solvent used.

In addition to the aforesaid effects of the present yellow couplers, the dyes obtained thereby have excellent spectral absorption characteristics and excellent in color developability and hence a photosensitive layer can be made thiner with the result that sharpness of the dye images obtained is enhanced.

Further, notwithstanding the enhanced color developability of the present yellow couplers, no color stain associated with the use of known yellow couplers is observed in the case of the present yellow couplers and such effect as decrease in fog density is attained thereby.

The color developing agent used in the present invention is an aromatic primary amine type compound, typical of which are those of p-aminophenol type or p-phenylenediamine type. Concretely, the developing agents of these types include, for example, p-aminophenol, diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)-toluene, N-ethyl-N-β- methanesulfonamidoethyl-3-methyl-4-aminoaniline sulfate, N-ethyl-N-β-methanesulfonamidoethyl-4-aminoaniline, 4-N-ethyl-N-β-hydroxyethylaminoaniline, N-ethyl-N-β-methoxyethyl-3-methyl-4-aminoaniline p-toluenesulfonate, N-ethyl-N-[2-(2-methoxyethoxy)ethyl]-3-methyl-4-aminoaniline p-toluenesulfonate, N-ethyl-N-{2-[-(2-methoxyethoxy)ethoxy]-ethyl}-3-methyl-4-4-aminoaniline-p-toluenesulfonate.

Furthermore, the present invention is applicabel to a variety of light-sensitive silver halide color photographic materials and also to those sensitive, for example, to ultraviolet rays, visible light, infrared light, X-ray, γ-ray or microwave.

The aforesaid color developing agents may be used either singly or in combination of two or more, and the color developer used in the present invention may optionally be incorporated with commonly used additives, for example, alkali agents such as sodium hydroxide, sodium carbonate, potassium carbonate, alkali metal sulfites, alkali metal bisulfites, alkali metal thiocyanates, alkali metal halides, benzyl alcohol, water softening agents, thickners, and development regulators such as citragine acid. This color developer usually has a pH value of above 7, most generally about 10 to about 13.

The color developing process may include a black-and-white developing process. A black-and-white developer used in the process is called a black-and-white first developer used in commonly known treatment of light-sensitive silver halide color photographic materials, or is a developer used in treatment of light-sensitive silver halide black-and-white photographic materials, and the developer may be incorporated with various well-known additives which are generally added to the black-and-white developer. Typical of the known additives are developing agents such as 1-phenyl-3-pyrazolidone, methol and hydroquinone, preservatives such as sulfites, promoters comprising alkalis such as sodium hydroxide, sodium carbonate, potassium carbonate and the like, organic or inorganic inhibitors such as potassium bromide, 2-methylbenzimidazole, methylbenzthiazole and the like, hard water softening agents such as polyphosphates, surface over development inhibitors comprising small amounts of iodides and mercapto compounds and the like additives.

In the process for forming dye images according to the present invention, after development, there may be carried out any treatment such as comprising bleaching, fixing or bleach-fixing, stabilizing, water-washing, stopping or the like in suitable combination.

The present yellow couplers may be incorporated, according to conventionally known procedures, into silver halide photographic emulsions to be used in light-sensitive silver halide color photographic materials. The resulting emulsion is coated on a support and then dried. In that case, the amount of the present yellow couplers to be incorporated into the emulsion may of course be varied according to the object for which the resulting light-sensitive color photographic material comprising the couplers is used, though it is generally preferable to use the couplers in an amount of 10 to 300 g per mole of silver halide.

Irrespective of kind and use thereof, any light-sensitive silver halide photographic materials are applicable to the dye image forming process according to the present invention. For instance, the present process is applicable to multilayered light-sensitive silver halide color photographic materials of the negative type, light-sensitive color print photographic materials, or particularly advantageously to light-sensitive color photographic materials for reversal color treatment. Silver halides used in that case are, for example, silver chloride, silver bromide, silver iodide, silver chlorobromide, silver iodobromide and silver chloroiodobromide, and these silver halides are formulated into silver halide emulsion according to any procedures known per se. The silver emulsions prepared in this manner may be, for example, so-called conversion emulsions, Lippmann's emulsions, covered grain emulsions or such as previously fogged optically or chemically, and these emulsions are suitably selected according to the kind and use of the light-sensitive photographic material intended to be prepared. Similarly, the kind, content and mixing ratio of the silver halides used, and average particle and size distribution of the silver halide particles may suitably selected according to the kind and use of the light-sensitive photographic material as desired.

These silver halides may be sensitized with chemical sensitizer and further be optically sensitized to the desired wavelength region with optical sensitizers, for example, cyanine dyes or merocyanine dyes.

The silver halide is dispersed in an appropriate binder such as gelatin and coated on a suitable support to form photosensitive layer.

Light-sensitive silver halide photographic materials may contain other couplers together with the present yellow couplers in order to form multicolor images. Useful as the other couplers in the above case are, for example, 5-pyrazolone type magenta couplers, phenol type or naphthol type cyan couplers, and there can also be used for automasking purposes in combination therewith azo type colored couplers osazone type compounds, and couplers of a type releasing a diffusible dye on development. In that case, it is sometimes desirable to use desired colorless couplers which is colorless before color development in combination with the above-mentioned masking couplers. In order to improve further the light-sensitive silver halide photographic materials in their photographic characteristics, such couplers as called competing coupler, DIR couplers and BAR couplers (Bleach Accelerator Releasing Couplers) can also be used in combination with a variety of couplers mentioned above.

The light-sensitive silver halide photographic materials are prepared by coating on a support a silver halide emulsion containing the present yellow couplers, which emulsion has been prepared in the manner above explained, and if necessary the silver halide emulsion is coated on the support together with a sub layer, intermediate layer, filter layer, curl inhibition layer or the like. Usable supports in that case include paper, laminated paper, films or sheets of such substrates as glass, cellulose acetate, cellulose nitrate, polyester, polycarbonate, polyamide, polystyrene, polyolefin and the like. These supports may be subjected to surface treatment such as hydrophilization treatment in various ways, for example, saponification, corona discharge, subbing for the purpose of improving adhesion between the support and the constitutive layer to be coated thereon.

The light-sensitive silver halide photographic material applied to the present process fundamentally comprises at least a support and thereon a photosensitive layer, however, generally comprises plural layers to be formed suitably on various positions relative to the support in the photographic material.

Furthermore, by virtue of incorporating an ultraviolet absorber into a light-sensitive silver halide photographic material having incorporated therein the present yellow couplers, the yellow image obtained therefrom can be further improved in durability.

The present invention is illustrated below more fully with reference to examples, but it should be construed that embodiments of the invention are not limited thereto.

EXAMPLE 1

The present yellow couplers previously exemplified by reference to their respective numbers, as shown in Table 1, and comparative yellow couplers as will be illustrated later, each $3.0 \times 10^{-2}$ mole, were individually added to a mixture of dibutyl phthalate in an amount corresponding to ½ of the weight of each yellow coupler and 40 ml of ethyl acetate, followed by heating at 50° C. to dissolve completely. The resulting solutions were individually mixed with 10 ml of a 10% aqueous solution of Alkanol-E (alkylnaphthalene sulfonate produced and sold by Du Pont Co., the same shall apply hereinafter) and 200 ml of a 5% aqueous gelatin solution, the resulting mixtures were individually fed several times to a colloid mill to prepare emulsified dispersions of the yellow couplers. Each of the dispersions was incorporated into 1000 ml of a gelatinous silver chlorobromide emulsion, coated on a polyethylene-laminated paper and then dried to a sample of light-sensitive silver halide color photographic material. This sample was wedgewise exposed to light in the usual way and processed in accordance with the following processing steps and prescriptions.

| | |
|---|---|
| Color development | 3 min. 30 sec. |
| Bleach-fixing | 1 min. 30 sec. |
| Water-washing | 2 min. 0 sec. |
| Stabilization | 1 min. 0 sec. |
| [Color developer] | |
| Benzyl alcohol | 1.0 ml |
| Sodium hexametaphosphate | 3.00 g |
| Anhydrous sodium sulfite | 1.85 g |
| Sodium bromide | 1.40 g |
| Potassium bromide | 0.50 g |
| Boric acid ($Na_2B_4O_7 \cdot 10 H_2O$) | 39.10 g |
| N-ethyl-N-2-(methanesulfonamidoethyl)-3-methyl-4-aminoaniline sulfate | 4.50 g |

Water is added to make 1 liter and adjusted to pH 10.3 with sodium hydroxide.

| | |
|---|---|
| [Bleach-fixing solution] | |
| Ammonium iron ethylenediaminetetraacetate | 61.0 g |
| Diammonium ethylenediaminetetraacetate | 5.0 g |
| Ammonium thiosulfate | 124.5 g |
| Sodium metabisulfite | 2.7 g |
| Water is added to make 1 liter and adjusted to pH 6.5. | |
| [Stabilizing solution] | |
| Glacial acetic acid (trihydrate) | 20 ml |

800 ml of distilled water is added and adjusted to pH 3.5–4.0, and then made 1 liter.

In order to examine light fastness of each dye image obtained by the color development of each sample, the dye image after irradiation for 100 hours with a xenon fade-O-meter was measured in the stability by obtaining a density after irradiation, based on the initial density of 1.0, as a residual dye ratio in percentage.

As shown in Table 1, it is understood that the dye images of the present invention obtained according to the abovementioned processing procedure are excellent in both color developability and light fastness.

TABLE 1

| Sample No. | Coupler | Fog | Speed | Maximum density | Light fastness (%) |
|---|---|---|---|---|---|
| 1 | Exemplified coupler (1) | 0.02 | 100 | 2.98 | 73 |
| 2 | Exemplified coupler (2) | 0.02 | 100 | 2.92 | 71 |
| 3 | Exemplified coupler (7) | 0.03 | 103 | 3.05 | 70 |
| 4 | Comparative coupler (A) | 0.03 | 93 | 2.01 | 68 |
| 5 | Comparative coupler (B) | 0.03 | 86 | 1.85 | 71 |
| 6 | Comparative coupler (C) | 0.03 | 86 | 2.08 | 75 |
| 7 | Comparative coupler (D) | 0.03 | 93 | 2.25 | 71 |
| 8 | Comparative coupler (E) | 0.04 | 103 | 2.76 | 31 |
| 9 | Comparative coupler (F) | 0.05 | 100 | 2.80 | 35 |
| 10 | Comparative coupler (G) | 0.03 | 93 | 2.64 | 82 |

In the above table, the speed (i.e. sensitivity) was represented by a relative value as measured by assuming 100 the speed of sample No. 1.

The comparative couplers used were those as illustrated below.

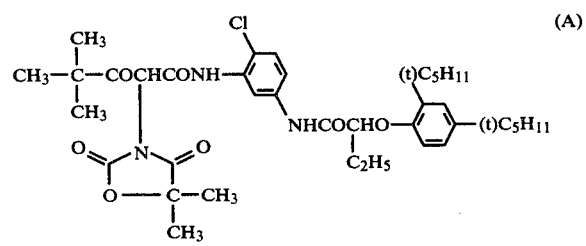

(This coupler is the same kind as that disclosed in Japanese Laid-Open-to-Public Publn. No. 66835/1973)

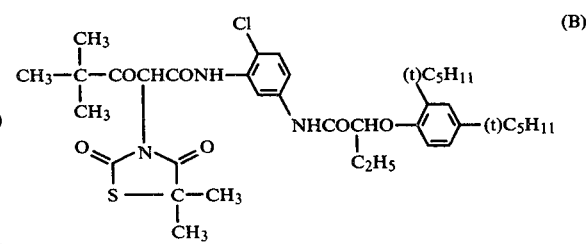

(This coupler is the same kind as that disclosed in Japanese Laid-Open-to-Public Publn. No. 94432/1973)

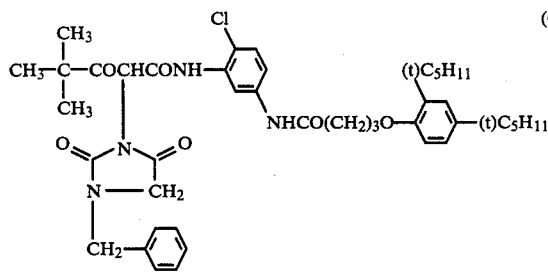

(C)

(This coupler is the same kind as that disclosed in Japanese Laid-Open-to-Public Publn. No. 29432/1973)

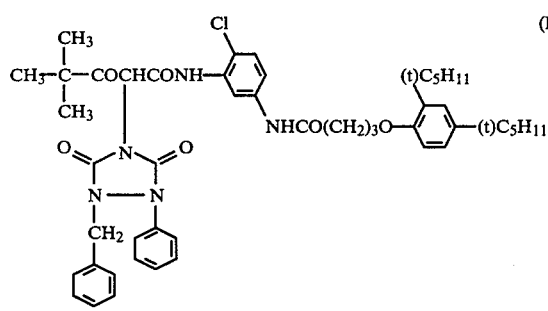

(D)

(This coupler is the same kind as that disclosed in Japanese Laid-Open-to-Public Publn. No. 66834/1973)

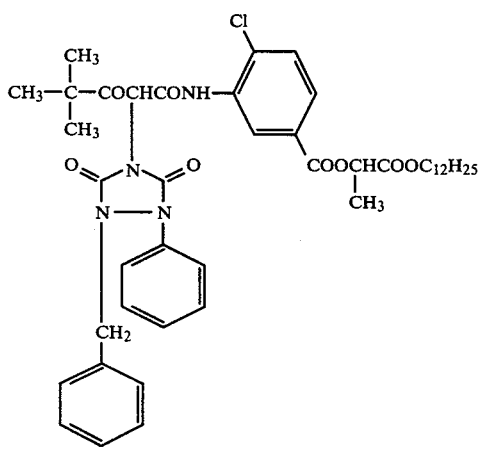

(E)

(This coupler is the same kind as that disclosed in Japanese Laid-Open-to-Public Publn. No. 66834/1973)

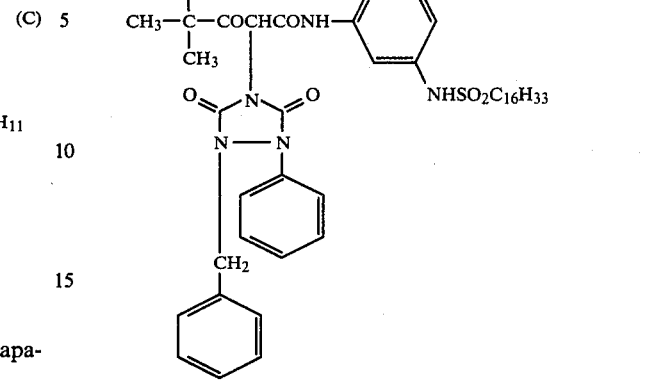

(F)

(This coupler is disclosed in Japanese Laid-Open-to-Public Publn. No. 115219/1977)

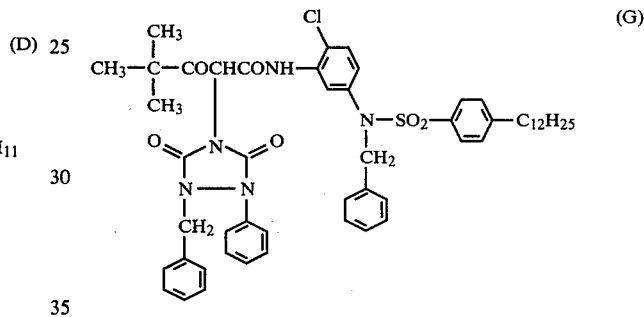

(G)

(This coupler is disclosed in Japanese Patent Application No. 27865/1978)

EXAMPLE 2

Emulsified coupler dispersions were prepared in the same manner as in Example 1, except that exemplified couplers (18), (19) and (27) were used in place of the exemplified couplers (1), (2) and (7) used in Example 1. The thus prepared dispersions were individually incorporated into 1000 ml of a high speed silver iodobromide emulsion (containing 4.0 mol% of selver iodide) and coated on a film base to prepare samples of light-sensitive silver halide color photographic material.

The samples thus prepared were wedgewise exposed to light and then processed according to the following processing steps and prescriptions.

| [Processing step] | (38° C.) | [Processing time] |
|---|---|---|
| Color development | | 3 min. 15 sec. |
| Bleaching | | 6 min. 30 sec. |
| Water-washing | | 3 min. 15 sec. |
| Fixing | | 6 min. 30 sec. |
| Stabilization | | 1 min. 30 sec. |

The processing solutions individually used in the abovementioned processing steps had the following their respective compositions.

| [Composition of color developer] | |
|---|---|
| 4-Amino-3-methyl-N-ethyl-N-($\beta$-hydroxyethyl)aniline sulfate | 4.75 g |

| [Composition of color developer] | |
|---|---|
| Anhydrous sodium sulfite | 4.25 g |
| Hydroxylamine ½sulfate | 2.0 g |
| Anhydrous potassium carbonate | 37.5 g |
| Sodium bromide | 1.3 g |
| Nitrilotriacetic acid trisodium salt (monohydrate) | 2.5 g |
| Potassium hydroxide | 10 g |

Water is added to make 1 liter and adjusted to pH 10.0 with potassium hydroxide.

| [Composition of bleaching solution] | |
|---|---|
| Ammonium iron ethylenediaminetetra-acetate | 100.0 g |
| Diammonium ethylenediaminetetra-acetate | 10.0 g |
| Ammonium bromide | 150.0 g |
| Glacial acetic acid | 10.0 ml |

Water is added to make 1 liter and adjusted to pH 6.0 with ammonia water.

| [Composition of fixing solution] | |
|---|---|
| Ammonium thiosulfate (50% aq. soln.) | 162 ml |
| Anhydrous sodium sulfite | 12.4 g |

Water is added to make 1 liter and adjusted to pH 6.5 with acetic acid.

| [Composition of stabilizing solution] | |
|---|---|
| Formalin (37% aq. soln.) | 5.0 ml |
| Konidax (produced by Konishiroku Photo Industry Co., Ltd.) | 7.5 ml |
| Water is added to make 1 liter. | |

As shown in Table 2, it is understood that the dye images of the present invention obtained by the processing under the above-mentioned conditions are excellent in color developability as well as in light fastness.

TABLE 2

| Sample No. | Coupler | Fog | Speed | Maximum density | Light fastness (%) |
|---|---|---|---|---|---|
| 11 | Exemplified coupler (18) | 0.13 | 100 | 3.34 | 66 |
| 12 | Exemplified coupler (19) | 0.15 | 103 | 3.40 | 65 |
| 13 | Exemplified coupler (27) | 0.13 | 94 | 3.31 | 68 |
| 14 | Comparative coupler (A) | 0.15 | 61 | 2.83 | 62 |
| 15 | Comparative coupler (B) | 0.15 | 55 | 2.56 | 60 |
| 16 | Comparative coupler (C) | 0.15 | 58 | 2.74 | 65 |
| 17 | Comparative coupler (D) | 0.14 | 72 | 3.09 | 62 |
| 18 | Comparative coupler (E) | 0.18 | 101 | 3.32 | 30 |
| 19 | Comparative coupler (F) | 0.20 | 95 | 3.42 | 28 |
| 20 | Comparative coupler (G) | 0.15 | 91 | 3.15 | 70 |

In the above table, the speed was represented by a relative value as measured by assuming as 100 the speed of sample No. 11.

EXAMPLE 3

In the same manner as in Example 1, samples of light-sensitive silver halide color photographic material were prepared, except that 4-equivalent yellow couplers as shown in Table 3 and as will be illustrated later were used in place of the yellow couplers used in Example 1, followed by the same treatments as in Example 1.

As shown in Table 3, it is understood that the coupler disclosed in Japanese Laid-Open-to-Public Publn. No. 24321/1972 is not a particularly excellent yellow coupler as compared with other 4-equivalent yellow couplers.

TABLE 3

| Sample No. | Coupler | Speed | Maximum density |
|---|---|---|---|
| 21 | Coupler (H) | 35 | 0.68 |
| 22 | Coupler (I) | 34 | 0.66 |
| 23 | Coupler (J) | 35 | 0.65 |
| 24 | Coupler (K) | 57 | 1.02 |
| 25 | Coupler (L) | 58 | 1.56 |

In the above table, the speed was represented by a relative value as measured by assuming as 100 the speed of sample No. 1 of Example 1.

The couplers used in this example, as shown in Table 3, were those as illustrated below.

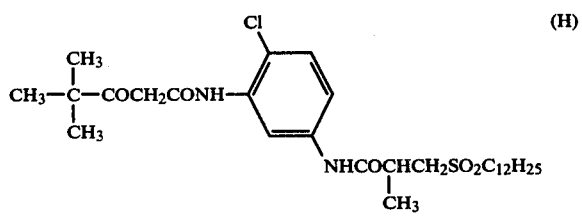
(H)

(This coupler is prepared in the same manner as in the exemplified coupler (1) of the present invention, except that the active point substitution component of the exemplified coupler (1) has been replaced by a hydrogen atom, i.e. a coupler disclosed in Japanese Laid-Open-to-Public Publn. No. 24321/1972)

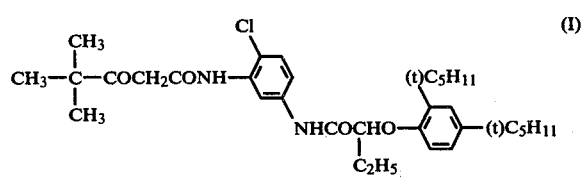
(I)

(This coupler is prepared in the same manner as in the comparative coupler (A) and (B), except that the active point substitution components of said comparative couplers have been individually replaced by a hydrogen atom.)

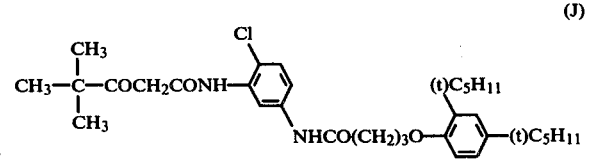
(J)

(This coupler is prepared in the same manner as in the comparative couplers (C) and (D), except that the active point substitution components of said comparative couplers have been individually replaced by a hydrogen stom.)

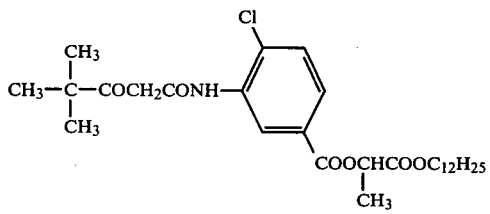 (K)

(This coupler is prepared in the same manner as in the comparative coupler (E), except that the active point substitution component of said comparative coupler has been replaced by a hydrogen atom, i.e. a coupler disclosed in Japanese Patent PUbln. No. 19031/1971.)

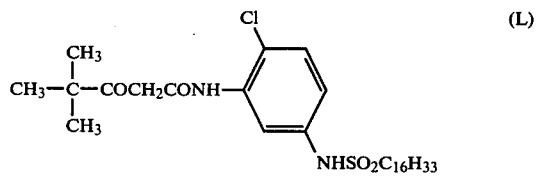 (L)

(This coupler is prepared in the same manner as in the comparative coupler (F), except that the active point substitution component of said comparative coupler has been replaced by a hydrogen atom.)

EXAMPLE 4

Samples of light-sensitive silver halide color photographic material were prepared in the same manner as in Example 1, except that exemplified coupler (1) and comparative coupler (D) were used and the amount of dibutyl phthalate used was varied as shown in Table 4, followed by the same treatments as in Example 1.

From the results as shown in Table 4, it is understood that the present yellow coupler are excellent in solubility and dispersion stability in the high boiling solvent and have stable color developability without being greatly influenced on photographic characteristic by changes in amount of the high boiling solvent used, in which the present yellow coupler has been dissolved and dispersed.

TABLE 4

| Sample No. | Coupler | DBP/coupler | Maximum density |
|---|---|---|---|
| 26 | Exemplified coupler (1) | ½ | 2.96 |
| 27 | Exemplified coupler (1) | ¼ | 2.97 |
| 28 | Exemplified coupler (1) | ⅛ | 2.94 |
| 29 | Comparative coupler (D) | ½ | 2.24 |
| 30 | Comparative coupler (D) | ¼ | 1.98 |
| 31 | Comparative coupler (D) | ⅛ | 1.65 |

In the above table, the DBP/coupler represents a value = (Number of grams of dibutyl phthalate used) / (Number of grams of coupler used)

EXAMPLE 5

Samples of light-sensitive silver halide color photographic material were prepared in the same manner as in Example 1, except that exemplified couplers (3) and comparative coupler (C) were used, the amount of dibutyl phthalate used was varied as shown in Table 5, and the amount of benzyl alcohol added to the color developer used in Example 1 was changed to 5.0 ml (i.e. the amount of benzyl alcohol usually used), followed by the same treatments as in Example 1.

From the results shown in Table 5, it is understood that in the same way as in Example 4, the present yellow coupler is excellent in solubility and dispersion stability in the high boiling solvent and has stable color developability without being greatly influenced on photographic characteristics by changes in amount of the high boiling solvent used, in which the present yellow coupler has been dissolved and dispersed.

TABLE 5

| Sample No. | Coupler | DBP/coupler | Maximum density |
|---|---|---|---|
| 32 | Exemplified coupler (3) | ½ | 2.95 |
| 33 | Exemplified coupler (3) | ¼ | 2.95 |
| 34 | Exemplified coupler (3) | ⅛ | 2.93 |
| 35 | Comparative coupler (C) | ½ | 2.88 |
| 36 | Comparative coupler (C) | ¼ | 2.65 |
| 37 | Comparative coupler (C) | ⅛ | 2.20 |

What we claim is:

1. A process for forming yellow dye images comprising developing an imagewise exposed light-sensitive silver halide photographic material with a developer containing an aromatic primary amine type developing agent in the presence of a yellow coupler represented by the following general formula (I):

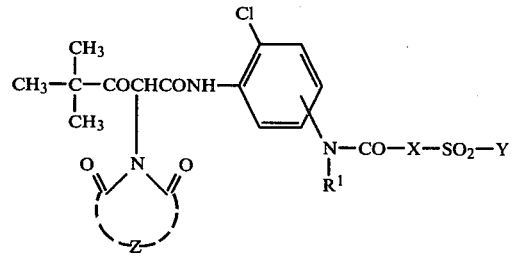

wherein $R^1$ represents a hydrogen atom or an alkyl group, aryl group or heterocyclic group, which may individually have a substituent, X represents an alkylene, arylene, aralkylene or divalent organic group represented by the following general formula (II) -A-V-B- which may individually have a substituent, Y represent an alkyl group; aryl group or heterocyclic residue, which may individually have a substituent, Z represents a non-metal atomic group necessary for forming in cooperation with —CO—N—CO— a 5- or 6-membered ring, wherein A and B individually represent an alkylene, a arylene or aralkylene group, which may individu- 2. A process for forming dye images according to claim 1, wherein the yellow coupler used is represented by the following general formula (III):

General formula (III)

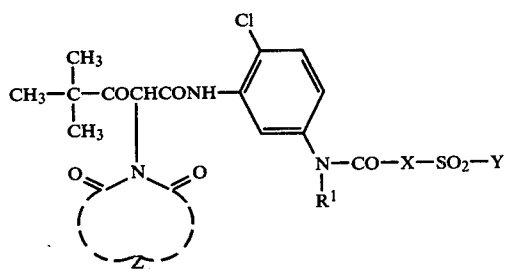

wherein $R^1$, X, Y and Z are individually as defined in claim 1:

3. A process for forming dye images according to claim 2, wherein $R^1$ in the general formula (III) is a hydrogen atom or an alkyl group which may have a substituent.

4. A process for forming dye images according to claim 2, wherein $R^1$ in the general formula (III) is a hydrogen atom.

5. A process for forming dye images according to claim 1, 2, 3 or 4, wherein X in the general (I) or (III) is an alkylene group which may have a substituent.

6. A process for forming dye images according to claim 1, 2, 3, 4 or 5, wherein Y in the general formula (I) or (III) is an alkyl or aryl group which may individually have a substituent.

7. A process according to claim 1, the developer contains no benzyl alcohol.

8. A photographic material having a light sensitive silver halide emulsion layer coated on a support wherein the material contains a yellow coupler represented by the following general formula (I):

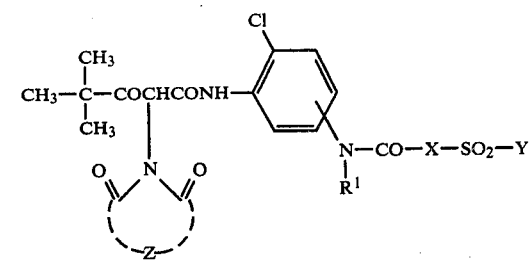

wherein $R^1$ represents a hydrogen atom or an alkyl group, aryl group or heterocyclic group, which may individually have a substituent, X represents an alkylene, arylene, aralkylene or divalent organic group represented by the following general formula (II), -A-V-B- which may individually have a substituent, Y represent an alkyl group, aryl group or heterocyclic residue, which may individually have a substituent, Z represents a non-metal atomic group necessary for forming in cooperation with —CO—N—CO— a 5- or 6-membered ring, wherein A and B individually represent an alkylene, arylene or aralkylene group, which may individually have a substituent, and V represents a divalent linking group.

9. A photographic material according to claim 8, wherein the yellow coupler used is represented by the following general formula (III):

General formula (III)

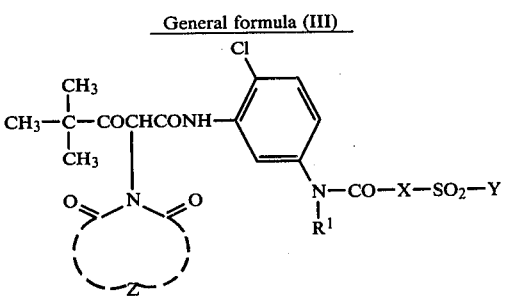

wherein $R^1$, X, Y and Z are individually as defined in claim 8.

10. A photographic material according to claim 9, wherein $R^1$ in the general formula (III) is a hydrogen atom or an alkyl group which may have a substituent.

11. A photographic material according to claim 9, wherein $R^1$ in the general formula (III) is a hydrogen atom.

12. A photographic material according to claim 8, wherein X in the general formula (I) is an alkylene group which may have a substituent.

13. A photographic material according to claim 8, wherein Y in the general formula (I) is an alkyl or aryl group which may individually have a substituent.

* * * * *